United States Patent
Zeng et al.

(10) Patent No.: US 11,946,069 B2
(45) Date of Patent: Apr. 2, 2024

(54) METHOD FOR GENERATING MULTIPLE CELLULAR PRODUCTS FROM SINGLE PLURIPOTENT CELL SOURCE

(71) Applicant: RxCell Inc., Novato, CA (US)

(72) Inventors: Xianmin Zeng, Novato, CA (US); Mahendra Rao, Timonium, MD (US)

(73) Assignee: RxCell, Inc., Novato, CA (US)

( * ) Notice: Subject to any disclaimer, the term of this patent is extended or adjusted under 35 U.S.C. 154(b) by 521 days.

(21) Appl. No.: 16/970,745

(22) PCT Filed: Mar. 11, 2019

(86) PCT No.: PCT/US2019/021555
§ 371 (c)(1),
(2) Date: Aug. 18, 2020

(87) PCT Pub. No.: WO2019/177936
PCT Pub. Date: Sep. 19, 2019

(65) Prior Publication Data
US 2021/0009945 A1    Jan. 14, 2021

Related U.S. Application Data

(60) Provisional application No. 62/641,570, filed on Mar. 12, 2018.

(51) Int. Cl.
| | | |
|---|---|---|
| *C12N 5/0735* | (2010.01) | |
| *C12N 5/071* | (2010.01) | |
| *C12N 5/0775* | (2010.01) | |
| *C12N 5/079* | (2010.01) | |
| *C12N 5/0793* | (2010.01) | |
| *C12N 5/0797* | (2010.01) | |

(52) U.S. Cl.
CPC ......... *C12N 5/0606* (2013.01); *C12N 5/0619* (2013.01); *C12N 5/0621* (2013.01); *C12N 5/0622* (2013.01); *C12N 5/0623* (2013.01); *C12N 5/0668* (2013.01); *C12N 5/067* (2013.01); *C12N 2506/03* (2013.01)

(58) Field of Classification Search
None
See application file for complete search history.

(56) References Cited

U.S. PATENT DOCUMENTS

2006/0018886 A1    1/2006    Klimanskaya et al. ..... 424/93.7

FOREIGN PATENT DOCUMENTS

| WO | 2017/106932 | 6/2017 |
| WO | 2017/121794 | 7/2017 |

OTHER PUBLICATIONS

Shi et al. "Induced pluripotent stem cell technology: a decade of progress." Feb. 2017, Nature Reviews Drug Discovery, vol. 16: 115-130. (Year: 2017).*
International Search Report and Written Opinion in PCT/US19/21555 dated May 24, 2019.
International Preliminary Report on Patentability in PCT/US19/21555 dated May 24, 2019.
Rao, M.S. & Atala, A. "Developing Induced Pluripotent Stem Cell-Based Therapy for the Masses" Stem Cells Translational Medicine 2016 5:129-131.
Chung et al. "Genetic and Epigenetic Instability of Human Pluripotent Stem Cells" The Open Stem Cell Journal 2011 3:52-61.
Kim et al. "Epigenetic memory in induced pluripotent stem cells" Nature 2010 467(7313):285-290.
McEwen et al. "The impact of culture on epigenetic properties of pluripotent stem cells and pre-implantation embryos" Biochem Soc Trans 2013 41(3):711-719.

* cited by examiner

*Primary Examiner* — Teresa E Knight
(74) *Attorney, Agent, or Firm* — Licata & Tyrrell P.C.

(57) ABSTRACT

Methods are provided for generating multiple cellular products via differentiation of cells from single clinically compliant pluripotent cells into multiple cellular products selected from retinal epithelium, retinal progenitors, neural stem cells, dopaminergic neurons, astrocytes, hepatocytes, endothelial cells and mesenchymal cells using standard differentiation protocols for the multiple cellular products.

8 Claims, 6 Drawing Sheets

Specification includes a Sequence Listing.

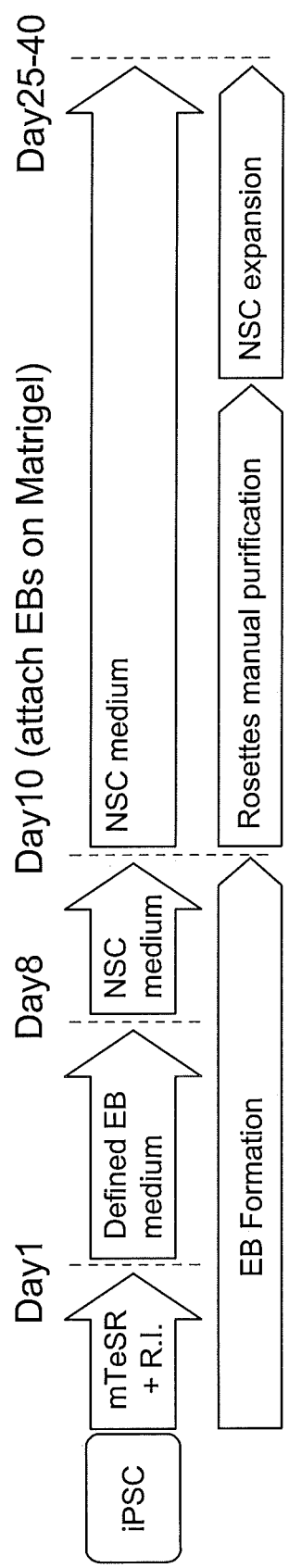
FIG. 1A
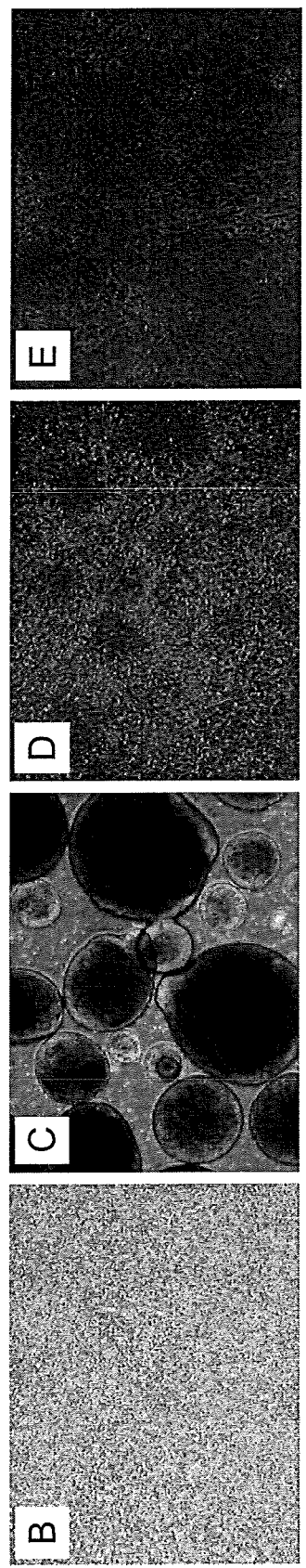
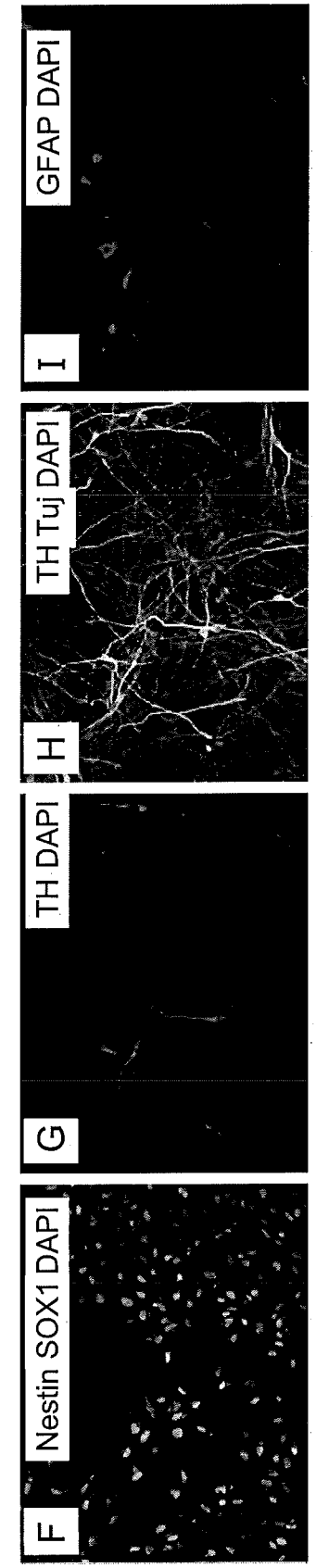
FIG. 1B-I

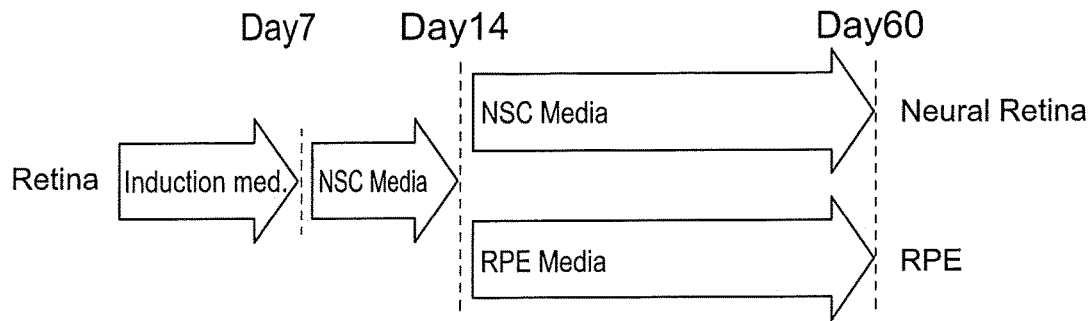
FIG. 2A
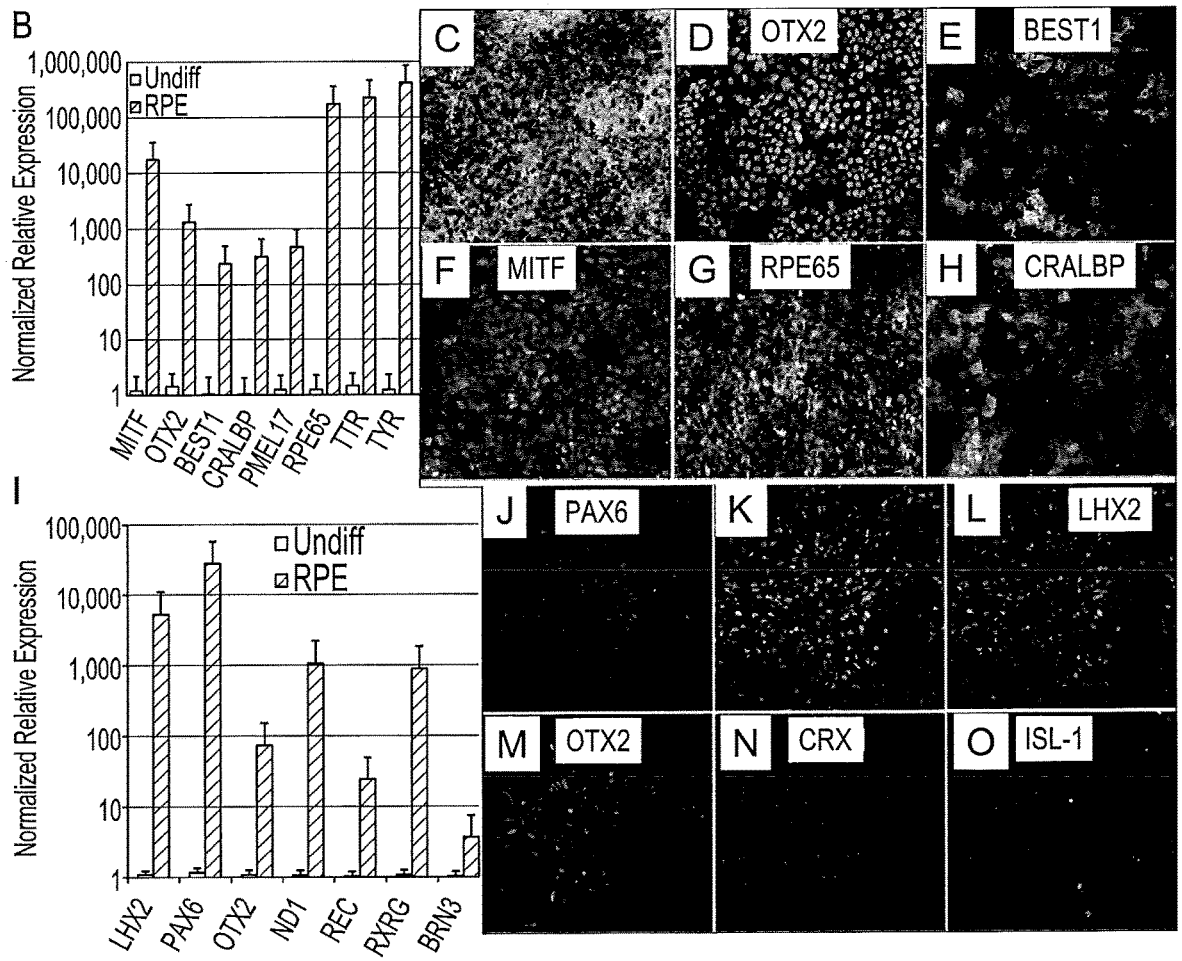
FIG. 2B-O

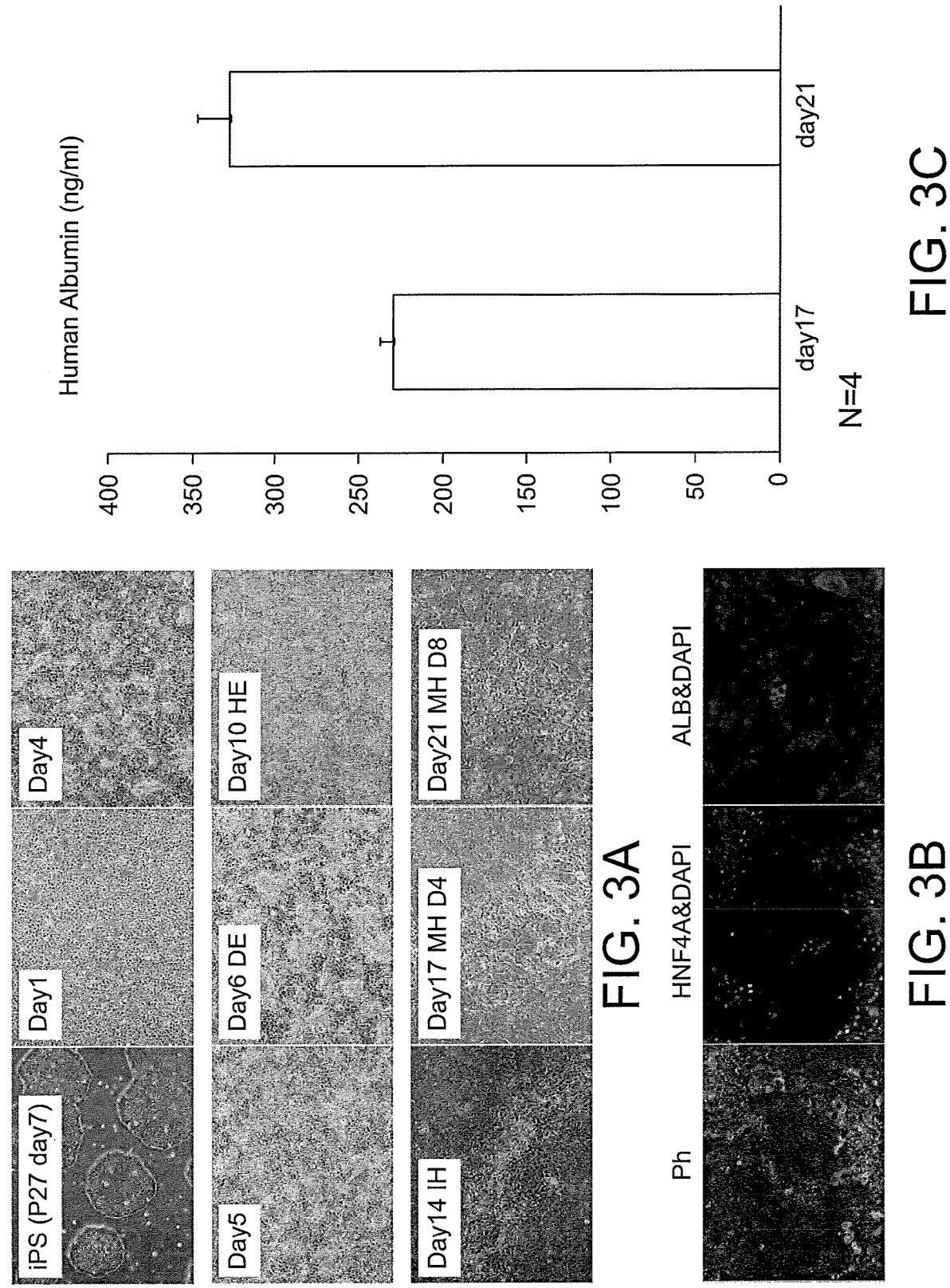

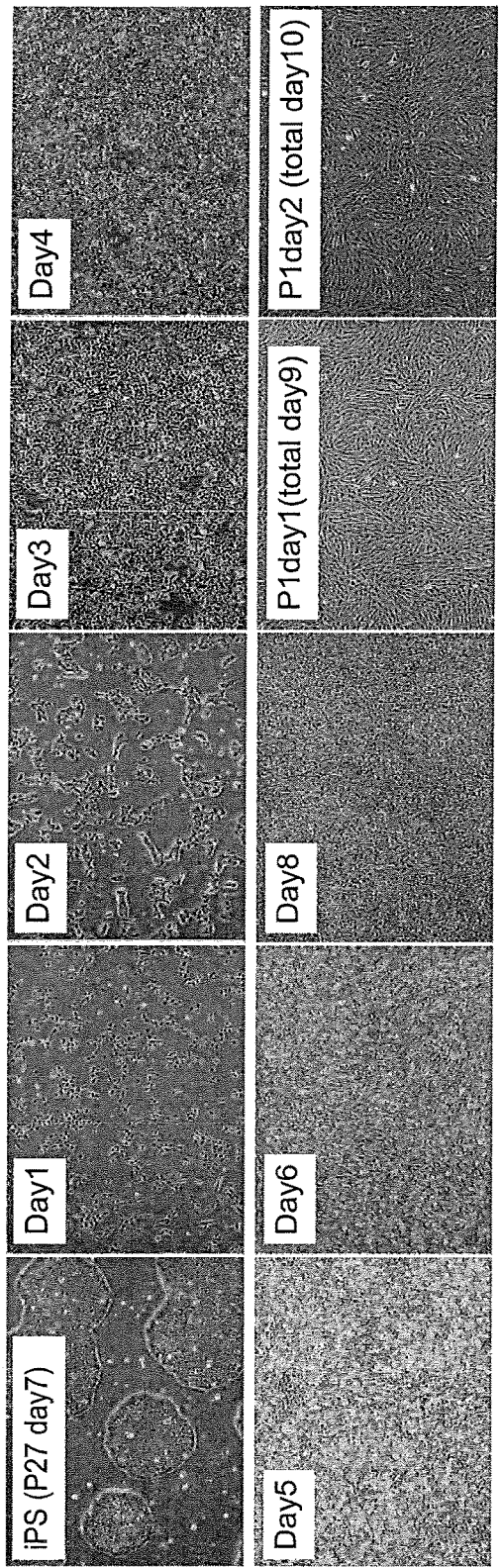
FIG. 5A
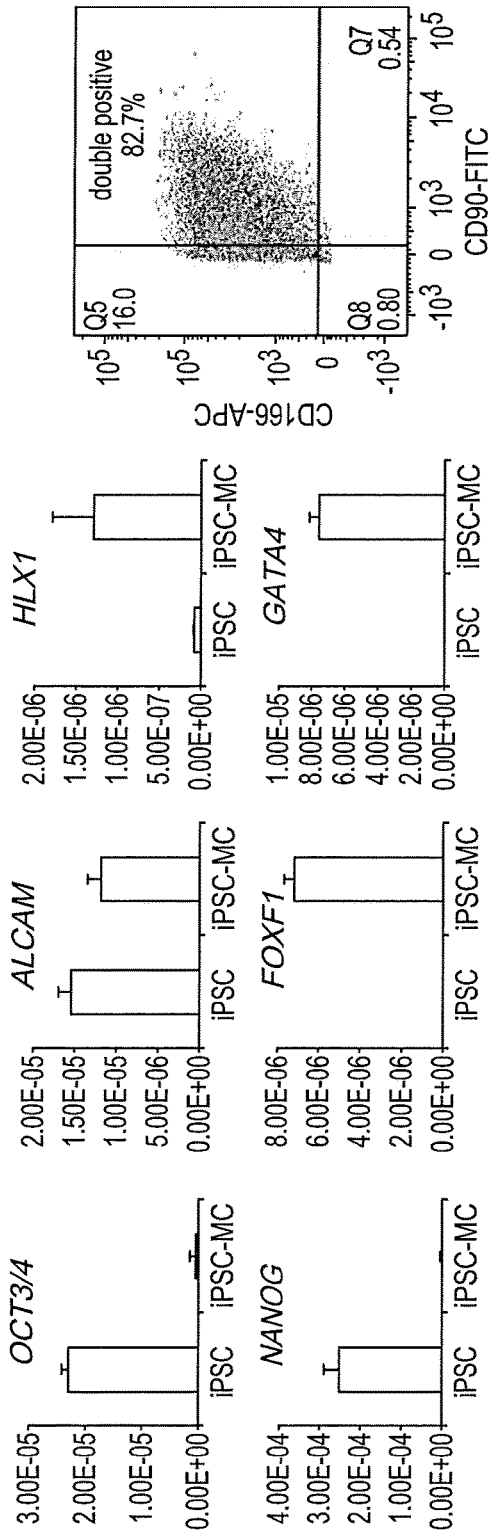
FIG. 5B
FIG. 5C

METHOD FOR GENERATING MULTIPLE CELLULAR PRODUCTS FROM SINGLE PLURIPOTENT CELL SOURCE

This patent application is the National Stage of International Application No. PCT/US2019/021555, filed Mar. 11, 2019, which claims the benefit of priority from U.S. Provisional Patent Application Ser. No. 62/641,570 filed Mar. 12, 2018, the contents of each of which are herein incorporated by reference in their entirety.

FIELD OF THE INVENTION

The present invention relates to methods for generating multiple cellular products by differentiation of cells from single clinically compliant pluripotent cells into, for example, retinal epithelium, retinal progenitors, neural stem cells, dopaminergic neurons, astrocytes, hepatocytes, endothelial cells and mesenchymal cells using standard differentiation protocols for the multiple cellular products.

BACKGROUND

Induced pluripotent stem cells (iPSC) and embryonic stem cells (ESC) can be distinguished from all other cells both in their ability to produce all major cell types in the body and to maintain their pluripotency over the lifespan of an individual. iPSCs have become the cell of choice for developing cellular products because of their relative ease in generation and standardization of technology and the availability of current good manufacture practice (cGMP) compatible lines In general, there are three models for utilization of induced pluripotent stem cell (iPSC) lines for therapy including allogeneic, autologous and an intermediate between these two referred to as hybrid HLA matched model.

Irrespective of the model proposed, the cost of iPSC based models has been considered prohibitive because if each line is considered a different starting material and each product is of course a different product for regulatory purposes, then every time a new line is made and a different process is used to manufacture the final product all the testing and safety studies and clinical studies would have to be repeated.

A second reason costs are high is mainly due to the long and often inefficient differentiation process. In addition, the testing programs and the level of rigor demanded on making allogeneic target lot (when applied to the manufacture of a small lot or a single dose) imposes a prohibitive per dose cost compared on cell therapy products (Rao and Atala, 2016). While alternate promising strategies for manufacture including automation, 3D methodologies and tissue printing techniques are being evaluated, these technologies do not necessarily reduce cost.

There is therefore a need for alternative, lower cost methodologies for alternative, lower cost methodologies for manufacture of cellular products from iPSCs.

SUMMARY OF THE INVENTION

The present invention provides a process for making multiple cell products from each iPSC line which consolidates the manufacturing process so that costs are reduced. By ensuring that clear intermediates are identified so that they can be segregated from other unwanted cell types for a particular indication, one can break up the manufacturing process into modules. Further by ensuring that these intermediates can be frozen, one can ensure that each modular process can be controlled independently from the others, thereby reducing the need to occupy a manufacturing suite over long time periods further substantially reducing cost. In addition, by using common robust processes, one can standardize manufacturing over multiple lines ensuring that there is comparability across different lines as required by regulatory authorities, thus further reducing the cost of manufacture.

Accordingly, an aspect of the present invention relates to methods for generating multiple cellular products from a single clinically compliant pluripotent cell source. Multiple cellular products which can be differentiated from the single clinically compliant pluripotent cell source in accordance with the present invention include retinal epithelium, retinal progenitors, neural stem cells, dopaminergic neurons, astrocytes, hepatocytes, endothelial cells and mesenchymal cells. The multiple cellular products are produced via standard differentiation protocols for the multiple cellular products.

In one nonlimiting embodiment, the generated multiple cellular products can be cells from the same germ layer. In another nonlimiting embodiment, the generated multiple cellular products are from different germ layers.

In one nonlimiting embodiment, using methods of the present invention, neural stem cells, retinal epithelium and retinal progenitors are produced from the same single clinically compliant iPSC cell line using clinically compliant material.

In one nonlimiting embodiment, using methods of the present invention, endothelial cells and mesenchymal cells are produced from the same single clinically compliant iPSC line.

In one nonlimiting embodiment, markers are used to select and distinguish between the multiple cellular products in their intermediate stages.

In one nonlimiting embodiment, cell surface and/or PCR based techniques are used for selective isolation for stage specific process development of the multiple cellular products.

Another aspect of the present invention provides for storage of generated cellular products at intermediate stages in a cryopreservation media.

Another aspect of the present invention relates to generation of transplantable cells.

BRIEF DESCRIPTION OF THE FIGURES

FIGS. 1A-1I show generation of neural stem cells (NSC) from a cGMP-compliant iPSC line referred to herein as NCL2 and subsequently differentiation into dopaminergic neurons and astrocytes. A schematic representation of the NSC derivation and differentiation process is depicted in FIG. 1A wherein confluent iPSC (FIG. 1B) were used to generate embryonic bodies (EB) (FIG. 1C). After culturing in defined EB medium for 8 days, EB were further cultured in NSC medium for 2 more days in suspension. Then EB were attached to Matrigel coated dishes and rosettes were observed 1-3 days post attachment (FIG. 1D). After several rounds of manual dissection and purification, clean rosettes were collected and accutased to generate a homologous population of NSC (FIG. 1E). Quality of the NSC were analyzed by immunohistochemistry using NSC specific markers Nestin and SOX1 (FIG. 1F). NSCs were then further differentiated into dopaminergic neurons (FIGS. 1G & 1H) which is stained with TH (FIG. 1G) and Tuj (FIG. 1H) antibodies or astrocytes which is stained with GFAP marker (FIG. 1I).

FIGS. 2A-2O show retinal induction of NCL2. FIG. 2A is a schematic describing the steps involved in protocol to generate neural retinal including photoreceptors, and RPE cells from iPSCs. FIG. 2B shows qRT-PCR analysis of RPE cells at the end of 60 days showing strong induction of various RPE-specific markers including MITF, BEST1, RPE65, and OTX2. FIG. 2C is a brightfield microscopy image showing pigment RPE cells with distinctive morphology. FIGS. 2D-2H show ICC analysis showing the presence of various RPE proteins including OTX2, BEST1, MITF, RPE65 and CRALBP confirming RPE generation. FIG. 2I shows qRT-PCR analysis of neural retinal cells at the end of 60 days showing strong induction of various retinal stem cell markers (PAX6, LHX2), photoreceptor markers (OTX2, NEUROD1 (ND1), RCVRN, RXRG) and ganglion cell marker (BRN3). FIGS. 2J-2O show ICC analysis at 60 days shows similar retinal cell marker, Pax6 (J), LHX2 (L) co-expressed in the same cells (merged view in K), as well as photoreceptor markers OTX2, CRX and inner retinal cell marker, ISL-1.

FIGS. 3A-3C show differentiation into hepatocyte-like cells. FIG. 3A shows time dependent microscopic observation of NCL2 iPSC-hepatocyte-like cells. FIG. 3B shows immunofluorescence staining of the hepatocyte markers (HNF4A and ALB). FIG. 3C shows ELISA-based quantification of human albumin detected from culture supernatant at day 17 and 21. Error bars represent the standard deviation (s.d.) from the values of 4 independent differentiation experiments.

FIG. 4A shows microscopic observation of NCL2 iPSC-EC. FIG. 4B shows RT-qPCR analysis of pluripotency markers (Oct3/4, Nanog) and the EC marker genes (Pecam1, Kdr, Cdh5, CD34) in iPSC-EC relative to undifferentiated. Error bars represent the s.d. from the values of 4 independent experiments. FIG. 4C shows FACS-based quantification of the endothelial differentiation markers (CD31 and CD144).

FIGS. 5A-5C show differentiation into mesenchyme cells. FIG. 5A shows microscopic observation of NCL2 iPSC-MC. FIG. 5B shows RT-qPCR analysis of pluripotency markers (Oct3/4, Nanog) and the MC marker genes (Alcam, FoxF1, Hlx1, Gata4) in iPSC-MC relative to undifferentiated. Error bars represent the s.d. from the values of 4 independent experiments. FIG. 5C shows FACS-based quantification of the MC differentiation markers (CD90 and CD166).

FIG. 6A shows an experimental strategy of generating NCL2-GFP line targeting the Chr.13 safe harbor site. Solid black triangles represent the loxP sites and triangles filled with diagonal lines represent Lox sites for RMCE. Testing primer sets for "Left" (Left arm integration test), "Right" (Right arm integration test) and "ORF" (WT ORF test) are also illustrated. FIG. 6B shows an example of one NCL2-GFP heterozyte clone validated by junction PCR. FIG. 6C is a representative example of a GFP-positive NCL2 iPSC clone.

DETAILED DESCRIPTION

Figure 4A:
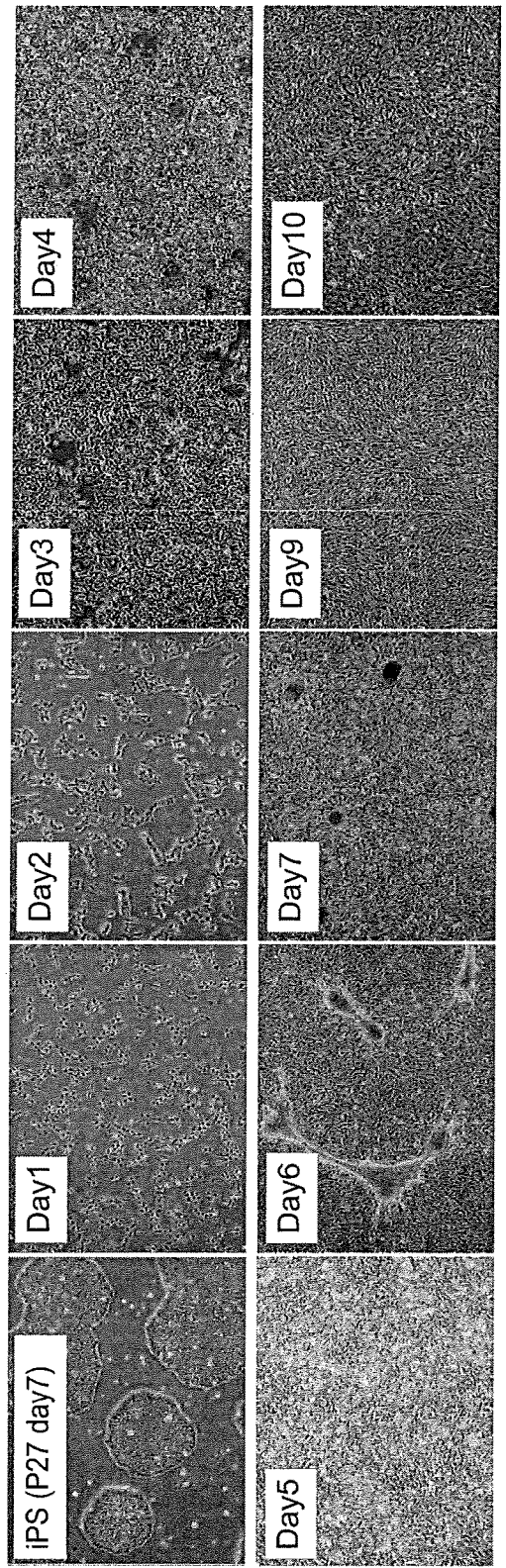
FIGS. 4A-4C show differentiation into endothelium-like cells.

Disclosed herein are methods for generating multiple cellular products from a single clinically compliant pluripotent cell source. iPSCs are unique in that they can make derivatives of all three germ layers and are believed to be truly immortal. Thus, the generated multiple cellular products can be cells from the same germ layer or from different germ layers. Nonlimiting examples of the multiple cellular products which can be differentiated from the single clinically compliant pluripotent cell source in accordance with the present invention include retinal epithelium, retinal progenitors, neural stem cells, dopaminergic neurons, astrocytes, hepatocytes, endothelial cells and mesenchymal cells. In one nonlimiting embodiment, using methods of the present invention, neural stem cells, retinal epithelium and retinal progenitors are produced from the same single clinically compliant iPSC cell line using clinically compliant material. In another nonlimiting embodiment, using methods of the present invention, endothelial cells and mesenchymal cells are produced from the same single clinically compliant iPSC line. In one nonlimiting embodiment, the transplantable cells are generated.

The multiple cellular products are produced from a single clinically compliant pluripotent cell source in accordance with the present invention via standard differentiation protocols for the multiple cellular products. In one nonlimiting embodiment, markers, nonlimiting examples of which are set forth in Tables 2 and 4 through 6 herein, are used to select and distinguish between the multiple cellular products in their intermediate stages. Further, cell surface and/or PCR based techniques using primers, nonlimiting examples of which are set forth in Table 3, are used for selective isolation for stage specific process development of the multiple cellular products.

These methods can be combined with various manufacturing technologies and are expected to significantly reduce the cost to manufacture multiple products from the same allogeneic iPSC line. In addition, using these methods, generated cellular products can be stored at intermediate stages in a cryopreservation media. Further, with gene editing techniques, it is possible to remove any immune mismatch by targeting the HLA locus as described, for example by Borger et al., 2016; Figueiredo and Blasczyk, 2015; and Torikai et al., 2013.

A clinically compliant line, referred to herein as NCL2 was prepared by a standardized cGMP-compliant protocol extensively characterized using comparability criteria that are under consideration by regulatory authorities (Baghbaderani et al., 2015). The ability of this cell line to differentiate into several major cell types that are being considered for therapeutics using generic standardized protocols that have been previously tested with multiple lines was assessed. As demonstrated herein, this cGMP-compliant iPSC line could be differentiated into neural derivatives including dopaminergic neurons, RPE and photoreceptors, as well as hepatocyte, endothelial and mesenchymal lineages. The goal in choosing these cell types was based on the fact that these are cell types that are being prioritized for cell-based therapy and that standard protocols have been described and optimized for each of these lineages. However, as will be understood be the skilled artisan upon reading this disclosure, other cellular products may be produced from the cGMP-compliant iPSCs as described herein.

In addition, a genetically modified subclone generated by standard genome editing techniques was produced and shown to behave similarly.

These demonstrations are indicative of cost effective iPSC derived cell based therapies.

cGMP-compliant induced pluripotent stem cell (iPSC) lines have been disclosed for clinical applications. Using methods of the present invention, the inventors herein have now found that multiple cellular products currently being considered for therapy can be generated from a single master cell bank of one of these clinically compliant iPSC lines. For example, using a stock at passage 20 prepared from the cGMP-compliant working cell bank (WCB), differentiation into therapeutic relevant cell types of the three germ layers using standardized but generic protocols was demonstrated. Cells generated include 1) neural stem cells, dopaminergic neurons and astrocytes, 2) retinal cells (RPE and photoreceptors) and 3) hepatocyte, endothelial and mesenchymal cells. These results and usefulness of the methods of the present invention were confirmed with a second clinically compliant line. The experiments disclosed herein confirm that well characterized IPSC lines have a broad potency and despite allelic variability the same protocols can be used with minimal modifications with multiple qualified lines. In addition, a constitutively expressed GFP cassette was introduced in Chr13 safe harbor site using a standardized method and no significant differences in growth and differentiation were observed between the engineered line and the control line indicating that engineered products can be made using the methods of the present invention.

A detailed characterization of NCL2, an iPSC line made with a cGMP-compliant manufacture process, was described previously by Baghbaderani et al., 2015. Additional assays/analyses performed on NCL2 are set forth in Table 1 including tests that are routinely performed on any cellular product such as sterility, presence of mycoplasma and endotoxin levels. In addition, STR based tracking as described by Reid et al., 2004 was used to ensure no sample mislabeling had occurred. To assess the quality of the line, the expression of pluripotency markers and their self-renewal capacity was examined. The stability of the cells in culture by analysis of their karyotype was also assessed. Since the ability to differentiate into multiple phenotypes is a hallmark of a pluripotent cell, a standardized embryoid body test was used to assess germ layer markers of differentiation including ectoderm, endoderm and mesoderm.

In addition to these tests, a comprehensive data set was developed for this line including: 1) whole genome sequencing analysis, 2) gene expression profiling by microarray and 3) comparative genomic hybridization and single nucleotide polymorphism analysis. This detailed characterization of the initial status of an iPSC line, which is theoretically immortal and may be used for years or even decades is important to this invention as it provides a data set for comparison with calibration materials and assists end users in determining which lines to use as a starting material for developing a therapeutic product. The detailed characterization also provides a reference to understand how a cell line may evolve over time or in different locations given the present invention's use of a common line to make multiple therapeutic products. It has been found that well characterized lines maintained in culture over more than 15 passages appear to lose their epigenetic memory and behave similarly to each other in their differentiation potential and response to growth factors despite their allelic differences.

To demonstrate suitability of a clinically compliant iPSC line such as NCL2 in making therapeutically relevant cell types of the central nervous system (CNS) in accordance with the present invention, a neural stem cell (NSC) stock was generated via a standard protocol used to generate NSC lines from more than 30 ESC or iPSC lines (Swistowski et al., 2009). There are several advantages in making and storing NSCs as an intermediate for manufacture of differentiated neural cell products, as these NSC are not position-specific, and can be expanded in vitro as well as differentiate into neurons of various subtypes including dopaminergic neurons, astrocytes and oligodendrocytes (Swistowski et al., 2010).

As shown in FIG. 1, NSC generated from NCL2 uniformly expressed Sox1 and nestin (FIG. 1F). Similar to other NSC lines derived by the same protocol, NCL2-derived NSCs can be cryopreserved and thawed with >90% recovery indicating that a generic protocol can be used to direct appropriate differentiation. No significant difference was seen between the differentiations of this line from any of the other lines using this protocol.

The ability of the NSCs to be differentiated into dopaminergic neurons was tested using a process developed for banking transplant ready dopaminergic neurons (Liu et al., 2013; Peng et al., 2014). As shown in FIGS. 1G and 1H, NCL2-derived NSCs differentiated into dopaminergic neurons and expressed TH similar to other lines in terms of timeline and efficiency.

The same stock of the NSCs was then tested for its ability to make astrocytes. FIG. 1I shows GFAP-expressing astrocytes after 35 days of differentiation using a standard protocol. No difference was observed between astrocyte differentiation of NCL2 and other lines such as described by Shaltouki et al., 2013 or with the second cGMP line tested.

In order to demonstrate the potency of these iPSC lines and confirm that the same WCB can be used to make a second product, a sample was taken from the same WCB and differentiated toward retinal derivatives. Cell from this line were treated with retinal induction media as described Zhu et al., 2017. Two weeks following treatment, the cells were either maintained in retinal induction media or RPE media. See FIG. 2A. Upon analysis of the cultures at 2 months following retinal induction, robust RPE and neural retina differentiation were observed by RT-PCR and IHC. RPE cultures showed characteristic hexagonal morphology and pigmentation as shown in FIG. 2C. Upon further analysis, cells were found to express key markers including OTX2, MITF, BEST1, RPE65, CRALBP, TTR and TYR by ICC and RT-PCR. See FIGS. 2B and 2D-2H. The neural retinal cultures consisted mainly of retinal progenitors at this stage expressing PAX6 and LHX2. See FIGS. 2J-2L. Cells expressing photoreceptor markers including OTX2, CRX, RCVRN, NEUROD1 and RXRG (see FIGS. 2I, 2M and 2N) and cells expressing ganglion cell markers, BRN3 and ISL-1 (see FIGS. 2I and 2O) were also observed. Further, it was demonstrated that SSEA1 staining can be used for sorting/enriching human retinal progenitors. SSEA3 and SSEA4, but not SSEA1 are expressed in undifferentiated human pluripotent stem cells including iPSCs. This is the opposite of undifferentiated mouse ESC/iPSCs which express SSEA1 but not SSEA3 and SSEA4. As the human iPSCs were induced to retinal lineage in accordance with the present invention, SSEA1 expression appeared. This expression decreases as the cells approach the retinal progenitor stage with 5- and 8-week retinal progenitors expressing CRX1, a marker for retinal progenitors/cells, but not SSEA1.

The potency and utility of these iPSC lines as starting material for the generation of endodermal and mesodermal derivatives was also evaluated via a number of protocols. The protocol described by Takebe et al. 2013 was used to test the ability of NCL line to differentiate into hepatocytes as this protocol can also be used to make hepatic buds in 3D cultures. Successful hepatocyte differentiation was initially evaluated by ELISA based quantification of human albumin in culture supernatant. The amounts of albumin were 231 and 329 ng/mL/24 hr at D17 and D21, respectively. See FIGS. 3A and 3C. Further, immunofluorescence staining confirmed the differentiation into hepatocyte-like cell, which are HNF4A and ALB positive. See FIG. 3B. No modification in the protocol was required and no optimization of the protocol was attempted, confirming that the protocol was robust and could be used with a well characterized iPSC lines in accordance with the present invention: A second iPSC line performed similarly.

Figure 4B:
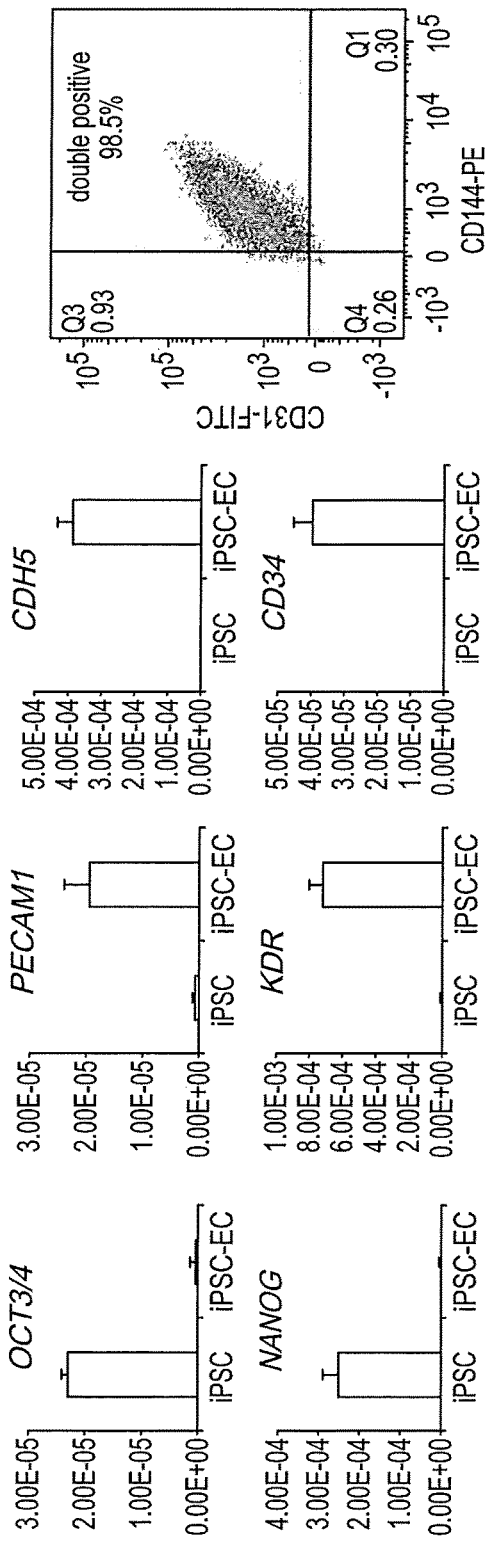
Figure 4C:
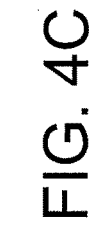

The ability of NCL2 to differentiate into endothelial cells was also demonstrated using the published protocol of Patsch et al., 2015. NCL2 iPSCs were differentiated into endothelial cells as detailed in the Examples section. See FIG. 4A. qRT-PCR analysis of differentiated cells showed expression of endothelial cell markers PECAM1, CDH5, KDR and CD34. See FIG. 4B. FACS based quantification analysis yielded over 98.5% of cells expressing both CD31 and CD144, indicating efficient EC differentiation potential. See FIG. 4C.

The ability of these iPSC lines to differentiate into a mesenchymal stem cell (MSC) like cells was also demonstrated using a protocol selected as it has been shown to generate MSC that can be used to stimulate hepatic organoid formation as well. FIG. 5A shows that NCL2 differentiated into cells with a uniform fibroblastic morphology resembling mesenchymal stem cells. qRT-PCR analysis confirmed the induction of mesenchymal cell markers including FOXF1, HLX1 and GATA4. See FIG. 5B. FACS analysis confirmed 82% of iPSC-MC expressed mesenchymal stem cell markers CD166 and CD90 (see FIG. 5C), and that these cells could be further differentiated into mesodermal derivatives.

Figure 6A:
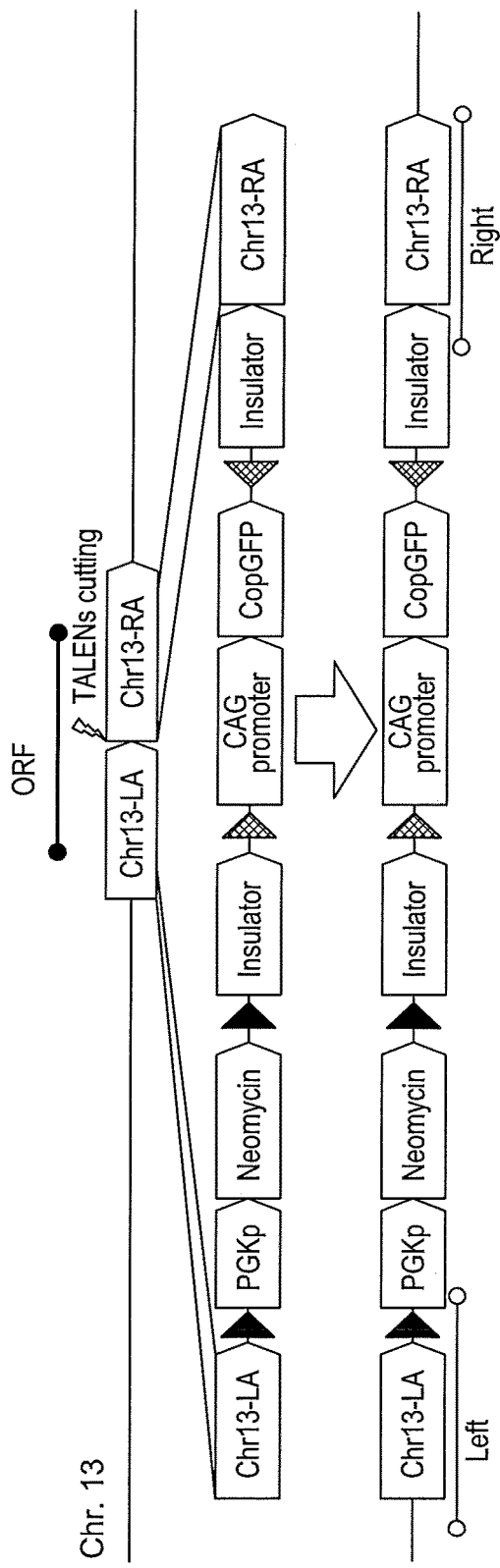
FIGS. 6A-6C show gene targeting at the Chr.13 safe harbor site.
Figure 6B:
Figure 6C:
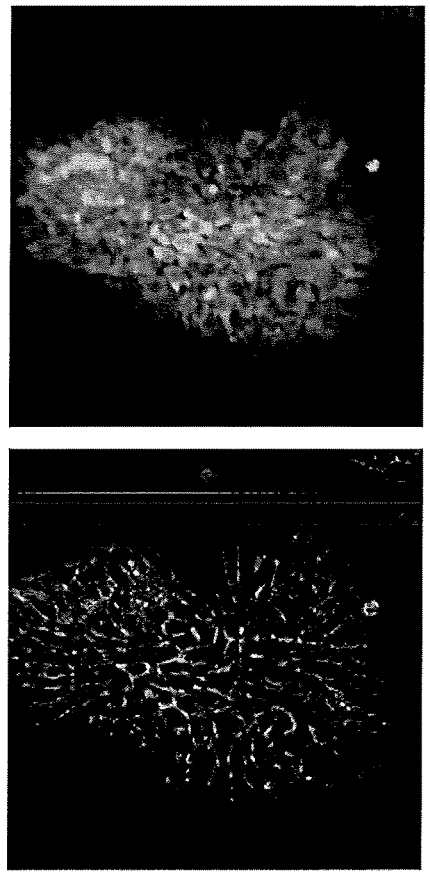

As gene editing of these iPSC lines is expected to be an important component of future therapy, an understanding if such editing would cause significant changes in behavior of the cells or alter their manufacturing is important. To test this, the Chr.13 safe harbor site in the NCL2 line was targeted and an engineered line NCL-GFP was generated which constitutively expresses GFP. This methodology was selected as it is a standardized protocol where previously characterized reagents can be used to target the same genetic locus as has been targeted previously. This process could then be validated for use with multiple input material (lines) as long as the process was reproducible. The constructs and the schemas of gene editing at the safe harbor site with the reporter (e.g. copGFP) driven by the constitutively active CAG promoter are illustrated in FIG. 6A and as previously reported by Pei et al., 2015. This targeting effort worked with similar efficiency as has been previously achieved with the same constructs and protocol. PCR confirmed the successful integration of donor constructs into appropriate genome loci. See FIG. 6B. A representative image of a NCL2-GFP iPSC clone is shown in FIG. 6C. No differences of the GFP-labeled line in terms of growth and differentiation ability compared to the parental line NCL2 were observed. This result was similar to what was observed with a previous line indicating that the safe harbor locus can be targeted reliably and sub clones can be expected to behave similarly.

Thus, as demonstrated herein, a single well-characterized, clinical grade iPSC line can be used in accordance with the present invention to make a variety of differentiated cell types using generic protocols. Instead of attempting to develop an individualized protocol optimized for one particular line, a clinical grade iPSC line was differentiated via standard published protocols merged into a unified protocol to differentiate cells into ectoderm, endoderm, mesoderm derivatives. Normal stages of differentiation that occur during normal development where ectoderm differentiates first followed by mes-endoderm which further differentiates to give ectoderm and mesoderm at the embryoid body stage were mimicked in culture. These lineages can be distinguished by the expression of characteristic lineage markers including cell surface markers. The ectoderm generates neuroectoderm which generates the CNS, PNS and the retina. This progressive restriction in cell fate generates intermediate progenitors that can be distinguished from each other and have been variously classified as tissue specific stem cells or progenitors.

As shown herein, retinal progenitors and retinal pigment epithelium as well as neural stem cells could be harvested from the same starting population using standardized protocols. Further, as shown herein, these intermediate stages could be distinguished from each other using stage specific PCR or antibody markers and the cells could be harvested and enriched to select for lineage specific progenitors. Nonlimiting examples of these markers are disclosed herein given for segregating neural, retinal and retinal pigment epithelium progenitors and segregating neuroectoderm from mesoderm and endoderm.

Further, to eliminate concerns of a particular line only working with a particular protocol, methods of the present invention involving a clinical grade iPSC line were evaluated with alternative differentiation protocols. In addition, two different clinical grade iPSC lines were evaluated and shown to differentiate into appropriate phenotypes (retinal derivatives and hepatocytes, endothelium and MSC) without any major modification of the protocols. These data are important as they are indicative that a well-characterized line that passes general evaluation criteria is usable in a standard protocol, and that the same starting material can be used to generate multiple products. This is critical to establish a process for replacing one MCB with another or using engineered sub clones derived from a parent line. The data herein indicates this to be a utility of pluripotent populations.

The results herein also provide important proof-of-principal for haplobanking or a personalized iPSC strategy. For haplobanking to be successful one needs to assume that multiple lines will behave similarly if they pass some acceptable criteria at the iPSC stage, and further that protocols which work with one line work with most other lines. Experiments were therefore designed to use protocols that had already been validated previously on an individual basis only, without generating a uniform robust protocol in accordance with the present invention, to harvest multiple lineages and intermediate progenitors.

In addition, it has been shown that engineering of iPSC cells expands there utility. Demonstration herein of engineered clinical grade iPSC lines retaining their pluripotential character and differentiating using the unified protocol similarly to the unengineered line and retaining of the engineered safe harbor site expression in the differentiated derivatives is therefore indicative of this expanded utility in the present invention.

Further, cellular products produced and identified in accordance with the present invention at intermediate stage can be frozen and thawed and used successfully for transplantation.

The following nonlimiting examples are provided to further illustrate the present invention.

EXAMPLES

Example 1: Human iPSC Culture

The cGMP-compliant human iPSC line NCL2 was generated from cord blood CD34+ cells by episomal vectors as described by Baghbaderani et al., 2015. Cells were cultured on Matrigel in mTeSR medium (Stem Cell Technologies) with 10 µM ROCK inhibitor Y-27632 and passaged with Accutase.

Example 2: Generation of NSC and Dopaminergic Differentiation

Generation of NSC from iPSC was performed as described by Swistowski et al., 2009. Confluent NCL2 cells were detached via collagenase and cultured in suspension as EBs in STEMPRO SFM medium (Life Tech.) supplemented with 100 nM LDN193189 (Stemgent), 10 µM SB431542 (Tocris), 2 µM Purmorphamine (Stemgent), 3 µM CHIR99021 (Stemgent), 100 ng/ml Sonic hedgehog (Peprotech) and 100 ng/ml FGF8 (Peprotech) for 8 days. EBs were directed towards neural lineages by the addition of FGF2 and allowed to attach in adherent cultures in NSC maintenance medium (XCell Science Inc.). After attachment, neural tube-like rosette structures were manually dissected and expanded in NSC maintenance medium.

Dopaminergic differentiation was carried out on culture dishes or glass cover slips coated with 2 mg/ml poly-L-ornithine (Sigma) and 10 mg/ml laminin (Life Tech.) using dopaminergic induction and maturation medium (XCell Science Inc.). More specifically, NSCs were cultured in dopaminergic induction medium supplemented with 200 ng/ml SHH with a medium change every other day for 8 days. Then cells were dissociated by accutase (Life Tech.) and passaged onto new poly-L-ornithine/laminin treated dishes in complete dopaminergic maturation medium for another 15-20 days with medium change every other day till the time of analysis.

Example 3: Neuro-Retinal and RPE Differentiation

Undifferentiated human iPSCs on Matrigel-coated plates were treated with retinal induction media containing 2 µM of IWR1 (Sigma Aldrich), 10 µM of 5B431542 (Stemgent), 100 nM of LDN193189 (Stemgent) and 10 ng/ml of human recombinant IGF1 (R&D Systems) for 5-7 days with daily medium change. Cells were then dissociated and passaged onto Matrigel-coated plates at a passaging ratio of 1:3 in Neural Stem Cell (NSC) medium that was comprised of DMEM/F-12 1:1 (HyClone), 0.5% Fetal Bovine Serum (FBS, Atlanta Biologicals), 1% Penicillin Streptomycin Amphotericin B (Lonza), 1% Sodium Pyruvate (Corning), 1% Sodium Bicarbonate (Corning), 1% HEPES Buffer (Corning), 1% MEM Non-essential Amino Acids (Corning) and 1% of N1 media supplement (Sigma Aldrich). The neuro-retinal stem cells were serially passaged using Accutase (Global Cell Solutions) at 1:3 ratio upon confluency. For RPE differentiation and maturation, cells at 2 weeks following induction were cultured in RPE medium that contained MEM/EBSS (HyClone) with 1% FBS, 1% Penicillin Streptomycin Amphotericin B, 1% Glutamax (Gibco), 0.25 mg/ml Taurine (Sigma Aldrich), 10 µg/ml Hydrocortisone (Sigma Aldrich) and 0.0065 µg/ml Triiodo-Thyronine (Sigma Aldrich) and 1% N1 media supplement indefinitely till the time of analysis.

Example 4: Endoderm Differentiation

For endodermal differentiation, undifferentiated human iPSCs were seeded on iMatrix-511™-coated plates and cultured in definitive endoderm induction medium (RPMI1640 with 2% B27 (Life Tech.), 100 ng/ml human activin A and 50 ng/ml human Wnt-3a (R&D Systems)) for 6 days. 500 µM Sodium butyrate (Sigma-Aldrich) was added from day1 to day3 of endoderm induction. Recombinant human activin A was kindly provided by Ajinomoto Co. For hepatic specification, human iPSC-derived endodermal cells were treated further with RPMI1640 with 2% B27 and 10 ng/ml human basic FGF (Wako) for 4 days. Subsequent hepatic maturation was induced by further treatment with HCM (Lonza, without EGF) containing 10 ng/ml HGF, 20 ng/ml human oncostatin M and 100 nM dexamethasone (Sigma-Aldrich) for 11 days.

Example 5: Endothelial (EC) and Mesenchymal (MC) Differentiation

For EC differentiation, the published protocol of Patsch et al., 2015 was adapted. NCL2 iPSCs were dissociated using Accutase and plated at a density of about 15,000 cells $cm^{-2}$ in StemFit™ with 10 µM ROCK inhibitor Y-27632. After one day, the medium was replaced with Mesoderm Induction Medium consisting of B27 medium (1:1 mixture of DMEM:F12 (1:1) with 1% Glutamax and 1% B27 and 1% Penicillin-Streptomycin (all Life Tech.) with 8 µM CHIR99021 (Tocris Bioscience) and 25 ng/ml BMP4 (R&D Systems)). After an additional three days, the Mesoderm Induction Medium was replaced with EC Induction Medium consisting of StemPro-34 SFM medium (Life Technologies) supplemented with 200 ng/ml VEGF (Life Technologies) and 2 µM forskolin (Sigma-Aldrich). The induction medium was renewed every day. After an additional 4 days, EC Induction Medium was replaced with EC Maintenance Medium consisting of StemPro-34 SFM medium supplemented with 50 ngml VEGF. At day 10 of differentiation, ECs were dissociated with Trypsin and subjected to FACS analysis.

For MC differentiation, NCL2 iPSCs were dissociated using Accutase and plated at a density of 15,000 cells $cm^{-2}$ in StemFit with 10 µM ROCK inhibitor Y-27632 for 1 day before induction. After the mesoderm induction as described above, the Mesoderm Induction Medium was replaced with mesenchymal cell differentiation medium A consistent with 1:1 mixture of DMEM:F12 (1:1) with 1% Glutamax and 1% B27 and 1% Penicillin-Streptomycin with 2 ng/ml activin A and 10 ng/ml PDGFBB (R&D Systems). After two days, induction medium A was replaced with induction medium B consistent with 1:1 mixture of DMEM:F12 (1:1) with 1% Glutamax and 1% B27 with 10 ng/ml FGF2 and 12 ng/ml BMP4 for additional two days. After passaging onto gelatin (Sigma-Aldrich)-coated dish, we maintained iPSC-MC with MSC-GM medium (Lonza). At day 10 of differentiation, MCs were dissociated with trypsin and subjected to FACS analysis.

Example 6: Immunocytochemistry

Immunocytochemistry and staining procedures were performed as described by Swistowska et al., 2010 and Zeng et al., 2003. Cells were fixed with 4% paraformaldehyde for 10 minutes, blocked in buffer containing 8% goat serum, 1% BSA, 0.1% Triton X-100 (all from Sigma) at room temperature for 1 h, followed by incubation with the primary antibody in blocking buffer at 4° C. overnight. Primary antibodies were detected using species-specific fluorescently labeled secondary antibodies (Life Tech.). All secondary antibodies were tested for cross reactivity and non-specific immunoreactivity.

Example 7: Genome Editing in Safe Harbor Locus on Chr13

Gene targeting by TALEN in safe harbor site on Chr.13 was performed as described by Pei et al., 2015. Specifically, 4-6 µg of a pair of TALEN RNA targeting Chr.13 safe harbor site were used for co-nucleofection with 10 µg donor vector Chr13-CAGp-copGFP using Amaxa Human Stem Cell Nucleofection Kit (Lonza). After nucleofection, cells were plated and selected by Puromycin (Life Tech.). Drug-resistant colonies were re-plated, and colonies growing from single cells that were uniformly green were selected manually under a fluorescent microscope. These selected clones were screened by PCR and sequencing to identify targets with correct donor vector integrations.

Tables

TABLE 1

Release assays and FYO tests for NCL2

| Assay | Objective | Evaluation criteria | Category |
|---|---|---|---|
| Pluripotency markers | Identity and Purity | SSEA-4 >70%, Tra-1-60 >70%, Tra-1-81 >70%, Oct3/4 >70%, Purity: CD34 <5% | Release Assay |
| Karyotypic Analysis | Safety | 46. XX or 46. XY | Release Assay |
| Mycoplasma testing | Safety | Negative | Release Assay |
| Endotoxin testing | Safety | Negative (<0.5 EU/ml) | Release Assay |
| Vector Clearance | Safety | No trace of residual plasmid | Release Assay |
| Sterility | Safety | Negative | Release Assay |
| Viral Panel Testing | Safety | Standard release panel | Release Assay |
| STR genotyping | Identity | Match starting population | Release Assay |
| Cell count and viability | Potency | % viability >50%; minimum cell number/vial | Release Assay |
| Gene array analysis | Identity and Potency | | Release Assay |
| Characterization Assays | | | |
| EB Formation | Potency | Germ layer differentiation | FIO |
| Gene Array analysis | Identity and Potency | Clustering with other IPSC and Pluritest or other relatedness assay | FIO |
| Colony Morphology | Identity and Purity | Characteristic morphology of iPSC colonies | FIO |
| Post thaw plating | Thawing efficiency and viability | 20+ colonies/vial after 7 days or 50% confluency | FIO |
| HLA Typing | Identity &Tracking | HLA-A. B, C, DRB1 and DQB1 | FIO |
| CGH & SNP array | Identity & Quality | Stability after multiple passages | FIO |

TABLE 2

List of primary antibodies used for distinguishing cells at different stages of retinal differentiation

| Target gene | species | Vendor | Dilution |
|---|---|---|---|
| GFP | Mouse | DSHB (GFP-G1, supernatant) | 1:100 |
| Biotinylated | Goat | R&D Systems | 1:250 |
| Otx2 | | | |
| Crx | Rabbit | AbCam | 1:100 |
| Aipl1 | Rabbit | Gift from Ramamurthy lab, WVU | 1:500 |
| Opsin (Ret-P1) | Mouse | Sigma Aldrich | 1:500 |
| Pax6 | Mouse | DHSB | 1:100 |
| Pax6 | Rabbit | Covance | 1:50 |
| Lhx2 | Goat | Santa Cruz Biotechnology | 1:100 |
| Recoverin | Rabbit | EMD Millipore Corp | 1:100 |
| SV2 | Mouse | DSHB | 1:100 |
| Brn3 | Goat | Santa Cruz Biotechnology | 1:200 |
| Nrl | Rabbit | R&D Systems | 1:200 |
| Trb2 | Goat | Santa Cruz Biotechnology | 1:100 |
| Cone arrestin | Rabbit | EMD Millipore | 1:100 |
| Islet1 | Mouse | DSHB | 1:20 |
| Blimp1 | Rat | Santa Cruz Biotechnology | 1:100 |
| RxRG | Rabbit | Santa Cruz Biotechnology | 1:100 |
| RPE65 | Mouse | Novus Biologicals | 1:100 |
| Bestrophin | Mouse | Santa Cruz Biotechnology | 1:100 |
| Human Nuclei | Mouse | EMD Millipore | 1:250 |
| Lamin B2 | Mouse | GeneTex | 1:500 |
| GFAP | Rabbit | Dako | 1:2000 |
| SSEA1 | Mouse | DHSB | 1:100 |
| SSEA3/4 | Mouse | Thermo Fisher Scientific | 1:50 |
| CD44 | Rat | DHSB | 1:100 |
| c-kit | ray | Thermofisher | 1:100 |

TABLE 3 qRT-PCR Primers for genes used for distinguishing cells at different stages of retinal differentiation

| Gene | Forward Sequence | Reverse Sequence |
|---|---|---|
| β-ACTIN | GGA TCA GCA AGC AGG AGT AT (SEQ ID NO: 1) | GGT GTA ACG CAA CTA AGT CAT AG (SEQ ID NO: 2) |
| OCT4 | GAG AAC AAT GAG AAC CTT CAG GA (SEQ ID NO: 3) | TTC TGG CGC CGG TTA CAG AAC CA (SEQ ID NO: 4) |
| RX | CTC CTC TCA GTT CAC CAA G (SEQ ID NO: 5) | CAT CTC TTT GCC TCA GTT CT (SEQ ID NO: 6) |
| PAX6 | ATC CGA GAT TTC AGA GCC C (SEQ ID NO: 7) | AGA CCA GAG GCA CTT ACT G (SEQ ID NO: 8) |
| LHX2 | TAC TAC AGG CGC TTC TCT G (SEQ ID NO: 9) | GAT AAA CCA AGT CCC GAG C (SEQ ID NO: 10) |
| MITF | CAG TAT GAC ATC ACG CAT CTT GC (SEQ ID NO: 11) | GCA CTC TCT GTT GCA TGA ACT (SEQ ID NO: 12) |

TABLE 3-continued qRT-PCR Primers for genes used for distinguishing cells at different stages of retinal differentiation

| Gene | Forward Sequence | Reverse Sequence |
| --- | --- | --- |
| CHX10 | CGA CAC AGG ACA ATC TTT ACC (SEQ ID NO: 13) | CAT AGA CGT CTG GGT AGT GG (SEQ ID NO: 14) |
| OTX2 | CCC ACT GTC AGA TCC CTT GT (SEQ ID NO: 15) | GGA AAG AGA AGC TGG GGA CT (SEQ ID NO: 16) |
| AIPL1 | TAA GGA ACC TGC AGA CCA AGG AG ((SEQ ID NO: 17) | GCA CTG GCA GTA GTT GAG GAT CAG (SEQ ID NO: 18) |
| BLIMP1 | GTG GTA TTG TCG GGA CTT TG (SEQ ID NO: 19) | GGT TGC TTT AGA CTG CTC TG (SEQ ID NO: 20) |
| CRX | CAC CGT GCT TGT GAT TTC AAC ACG A (SEQ ID NO: 21) | AAA CTC GTG TTG AAA TCA CAA GCA C (SEQ ID NO: 22) |
| RXRγ | CAT GAA GAG GGA AGC TGT G (SEQ ID NO: 23) | CCA CTG GTA GCA CAT TCT G (SEQ ID NO: 24) |
| RCVRN | CCA GAG CAT GTA CGC CAA CT (SEQ ID NO: 25) | CAC GTC GTA GAG GGA GAA GG (SEQ ID NO: 26) |
| BEST1 | CAT CCG CTT TAT TTA TAG GCT G (SEQ ID NO: 27) | TAG CTG TCG CAA TAC AGA G (SEQ ID NO: 28) |
| RPE65 | GCC TTG GAA GAA GAT GAT GGT GTA (SEQ ID NO: 29) | CCT TGG CAT TCA GAA TCA GGA GAT (SEQ ID NO: 30) |
| PMEL17 | CTC AGC CTT CAC CAT TAC T (SEQ ID NO: 31) | TTC TCA GGA AGT GCT TGT T (SEQ ID NO: 32) |
| TYR | CTA AGA ACC TGA TGG AGA AG (SEQ ID NO: 33) | GCA TTG GAC AGA AGG ATA T (SEQ ID NO: 34) |
| ALDH1A3 | TACAACGCCCTCTATGCAC (SEQ ID NO: 35) | CAAAGCGTATTCACCTAGTTCTC (SEQ ID NO: 36) |
| BMP4 | AGCACTGGTCTTGAGTATCC (SEQ ID NO: 37) | CTCCAGATGTTCTTCGTGGT (SEQ ID NO: 38) |
| PRNP | AGAGCAGTCATTATGGCGA (SEQ ID NO: 39) | CAGTGTTCCATCCTCCAGG (SEQ ID NO: 40) |
| RDH5 | GATGCACGTTAAGGAAGCAG (SEQ ID NO: 41) | ATGATACCAGCCACACCAG (SEQ ID NO: 42) |
| SIL1 | TCTAGGATGGCTCCTCTGG (SEQ ID NO: 43) | GCAAACTCCTTCAGGTTCTG (SEQ ID NO: 44) |
| SLC4A2 | ATTCCTGAGAATGCCGAGG (SEQ ID NO: 45) | TCCATGTTGGCACTACTCG (SEQ ID NO: 46) |
| TIMP3 | AGCAGATGAAGATGTACCGAG (SEQ ID NO: 47) | CACAGAGACTCTCGGAAGC (SEQ ID NO: 48) |
| TTR | GGACTGGTATTTGTGTCTGAG (SEQ ID NO: 49) | TCAGAGGACACTTGGATTCAC (SEQ ID NO: 50) |
| TYPR | AATTCAATGGCCAAGTCGG (SEQ ID NO: 51) | AGTGCAACCAGTAACAAAGC (SEQ ID NO: 52) |
| CRALBP | ACC TTT GAT GAG ATC TTG CAG (SEQ ID NO: 53) | GAA GCC ATT GAT TTG AGT TTC C (SEQ ID NO: 54) |
| SIX3 | GGA ATG TGA TGT ATG ATA GCC (SEQ ID NO: 55) | TGA TTT CGG TTT GTT CTG G (SEQ ID NO: 56) |
| THRB (C) | TTA CAG CGG TTG TGA TGC TC (SEQ ID NO: 57) | GGC CAT GTC CAA GTC AGA GT (SEQ ID NO: 58) |
| Cone arrestin (C) | CCC AGA GCT TTG CAG TAA CC (SEQ ID NO: 59) | CAC AGG ACA CCA TCA GGT TG (SEQ ID NO: 60) |
| GNAT2 (Cone) | TAA TGA CTC CGC ATC TTA CTA CC (SEQ ID NO: 61) | AGC ACA TCT TGC TCA CTA GG (SEQ ID NO: 62) |

TABLE 3-continued qRT-PCR Primers for genes used for distinguishing
cells at different stages of retinal differentiation

| Gene | Forward Sequence | Reverse Sequence |
|---|---|---|
| NRL (R) | TTC AGT CTC CTG GGA AGC TGT G (SEQ ID NO: 63) | TGC ACT TCA GAA ATG GCC GAG AG (SEQ ID NO: 64) |
| PDE6 (C/R) | CTC CCA AGT TCA AGC AGA G (SEQ ID NO: 65) | TGT CAT CTC CAA ATC CTT TCA C (SEQ ID NO: 66) |
| SOX2 | CGG ATT ATA AAT ACC GGC CC (SEQ ID NO: 67) | GTG TAC TTA TCC TTC TTC ATG AGC (SEQ ID NO: 68) |
| NANOG | CGG TTC ATC ATG GTA CAG TC (SEQ ID NO: 69) | CAG GAG TTT GAG GGT AGC TC (SEQ ID NO: 70) |
| SSEA4 | TGG ACG GGC ACA ACT TCA TC (SEQ ID NO: 71) | GGG CAG GTT CTT GGC ACT CT (SEQ ID NO: 72) |
| NESTIN | GGG AAG AGG TGAT GGA ACC A (SEQ ID NO: 73) | AAG CCC TGA ACC CTC TTT GC (SEQ ID NO: 74) |
| SOX1 | TCC CCC GCG TGA ACT G (SEQ ID NO: 75) | CAA GGC ATT TTG CGT TCA CA (SEQ ID NO: 76) |
| CD44 | CCACAGCCTCCTTTCAATAACC (SEQ ID NO: 77) | GGAGTCTTCGCTTGGGGTA (SEQ ID NO: 78) |
| PRDM1 | GGG ACT TTG CAG AAA GGC TTC AC (SEQ ID NO: 79) | AGA CTG CTC TGT GTT TGT GTG AG (SEQ ID NO: 80) |

TABLE 4

Stage-specific markers to distinguish
NSC of the CNS from neuro retinal NSC

| STAGE | NSC (CNS) | NSC (Eye field) |
|---|---|---|
| Eye field-optic cup stage (7-21 days following retinal induction) | NESTIN+, RX−, SOX1+, LHX2−, SIX3+, MITF−, PAX6+ | NESTIN+, RX+, SOX1−, LHX2+, PAX6+, SIX3+, OTX2+, MITF+ (give rise to both retinal progenitor cells and RPE precursors) |
| Retinal progenitor stage (21-42 days following retinal induction) | Eye Markers absent in CNS NSC | RX+, PAX6+, LHX2+, OTX2+, CHX10+ |
| Retinal photoreceptor precursors (60 days following retinal induction) | | OTX2+, CRX+, PRDM1+, THRB (C)+, RXRG (C)+, RECOVERIN+ |

TABLE 5

Markers that are 1) common and 2) different
for RPE precursor and retinal progenitor

| | Retinal progenitors | RPE progenitors |
|---|---|---|
| Common markers | OTX2+, PAX6+ | OTX2+, PAX6+ |
| Specific markers | RX+, CHX10+, LHX2 | MITF+, ZO-1+ BEST1, RPE65 and CRALBP+ (RPE cells) |

TABLE 6

Surface markers for sorting/selection
(human iPSC derived retinal cells)

| | iPSC | CNS NSC | Retinal NSC | RPE |
|---|---|---|---|---|
| SSEA1 | − | + | + | − |
| SSEA3/4 | + | − | − | − |
| CD44 | − | − | − | + |
| c-kit | − | + | + | − |
| CD29 | + | − | + | − |

What is claimed is:

1. A method for generating multiple cellular products, said method comprising differentiating cells from a single clinically compliant allogeneic induced pluripotent stem cell (iPSC) source from a stock at at least passage 20 or greater and made via a good manufacture process(GMP)-compliant manufacture process into multiple cellular products selected from retinal epithelium, retinal progenitors, neural stem cells, dopaminergic neurons, astrocytes, hepatocytes, endothelial cells and mesenchymal cells via generic; standard, published differentiation protocols for the multiple cellular products.

2. The method of claim 1 wherein the generated multiple cellular products can be cells from the same germ layer or three different germ layers.

3. The method of claim 1 wherein neural stem cells, retinal epithelium and retinal progenitors are produced from the same single clinically compliant iPSC cell line using clinically compliant material.

4. The method of claim 1 wherein endothelial cells and mesenchymal cells are produced from the same single clinically compliant iPSC line.

5. The method of claim 1 wherein the generated cellular products are stored at intermediate stages in a cryopreservation media.

6. The method of claim 1 wherein transplantable cells are generated.

7. The method of claim 1 further comprising using markers to select and distinguish between the multiple cellular products in their intermediate stages.

8. The method of claim 7 wherein cell surface and/or PCR based techniques are used for selective isolation for stage specific process development.

* * * * *

SEQUENCE LISTING

<160> NUMBER OF SEQ IDS NOS: 80

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1

```
ggatcagcaa gcaggagtat                                                    20

<210> SEQ ID NO 2
<211> LENGTH: 23
<212> TYPE: DNA
<213> ORGANISM: Artificial sequence
<220> FEATURE:
<223> OTHER INFORMATION: Synthetic

<400> SEQUENCE: 2
ggtgtaacgc aactaagtca tag                                                23

<210> SEQ ID NO 3
<211> LENGTH: 23
<212> TYPE: DNA
<213> ORGANISM: Artificial sequence
<220> FEATURE:
<223> OTHER INFORMATION: Synthetic

<400> SEQUENCE: 3
gagaacaatg agaaccttca gga                                                23

<210> SEQ ID NO 4
<211> LENGTH: 23
<212> TYPE: DNA
<213> ORGANISM: Artificial sequence
<220> FEATURE:
<223> OTHER INFORMATION: Synthetic

<400> SEQUENCE: 4
ttctggcgcc ggttacagaa cca                                                23

<210> SEQ ID NO 5
<211> LENGTH: 19
<212> TYPE: DNA
<213> ORGANISM: Artificial sequence
<220> FEATURE:
<223> OTHER INFORMATION: Synthetic

<400> SEQUENCE: 5
ctcctctcag ttcaccaag                                                     19

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
catctctttg cctcagttct                                                    20

<210> SEQ ID NO 7
<211> LENGTH: 19
<212> TYPE: DNA
<213> ORGANISM: Artificial sequence
<220> FEATURE:
<223> OTHER INFORMATION: Synthetic

<400> SEQUENCE: 7
atccgagatt tcagagccc                                                     19

<210> SEQ ID NO 8
<211> LENGTH: 19
<212> TYPE: DNA
<213> ORGANISM: Artificial sequence
```

```
<220> FEATURE:
<223> OTHER INFORMATION: Synthetic

<400> SEQUENCE: 8
agaccagagg cacttactg                                                     19

<210> SEQ ID NO 9
<211> LENGTH: 19
<212> TYPE: DNA
<213> ORGANISM: Artificial sequence
<220> FEATURE:
<223> OTHER INFORMATION: Synthetic

<400> SEQUENCE: 9
tactacaggc gcttctctg                                                     19

<210> SEQ ID NO 10
<211> LENGTH: 19
<212> TYPE: DNA
<213> ORGANISM: Artificial sequence
<220> FEATURE:
<223> OTHER INFORMATION: Synthetic

<400> SEQUENCE: 10
gataaaccaa gtcccgagc                                                     19

<210> SEQ ID NO 11
<211> LENGTH: 23
<212> TYPE: DNA
<213> ORGANISM: Artificial sequence
<220> FEATURE:
<223> OTHER INFORMATION: Synthetic

<400> SEQUENCE: 11
cagtatgaca tcacgcatct tgc                                                23

<210> SEQ ID NO 12
<211> LENGTH: 21
<212> TYPE: DNA
<213> ORGANISM: Artificial sequence
<220> FEATURE:
<223> OTHER INFORMATION: Synthetic

<400> SEQUENCE: 12
gcactctctg ttgcatgaac t                                                  21

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
cgacacagga caatctttac c                                                  21

<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
catagacgtc tgggtagtgg                                                    20
```

```
<210> SEQ ID NO 15
<211> LENGTH: 20
<212> TYPE: DNA
<213> ORGANISM: Artificial sequence
<220> FEATURE:
<223> OTHER INFORMATION: Synthetic

<400> SEQUENCE: 15
cccactgtca gatcccttgt                                                   20

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
ggaaagagaa gctggggact                                                   20

<210> SEQ ID NO 17
<211> LENGTH: 23
<212> TYPE: DNA
<213> ORGANISM: Artificial sequence
<220> FEATURE:
<223> OTHER INFORMATION: Synthetic

<400> SEQUENCE: 17
taaggaacct gcagaccaag gag                                               23

<210> SEQ ID NO 18
<211> LENGTH: 24
<212> TYPE: DNA
<213> ORGANISM: Artificial sequence
<220> FEATURE:
<223> OTHER INFORMATION: Synthetic

<400> SEQUENCE: 18
gcactggcag tagttgagga tcag                                              24

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
gtggtattgt cgggactttg                                                   20

<210> SEQ ID NO 20
<211> LENGTH: 20
<212> TYPE: DNA
<213> ORGANISM: Artificial sequence
<220> FEATURE:
<223> OTHER INFORMATION: Synthetic

<400> SEQUENCE: 20
ggttgcttta gactgctctg                                                   20

<210> SEQ ID NO 21
<211> LENGTH: 25
<212> TYPE: DNA
<213> ORGANISM: Artificial sequence
<220> FEATURE:
<223> OTHER INFORMATION: Synthetic
```

<400> SEQUENCE: 21
caccgtgctt gtgatttcaa cacga                                       25

<210> SEQ ID NO 22
<211> LENGTH: 25
<212> TYPE: DNA
<213> ORGANISM: Artificial sequence
<220> FEATURE:
<223> OTHER INFORMATION: Synthetic

<400> SEQUENCE: 22
aaactcgtgt tgaaatcaca agcac                                       25

<210> SEQ ID NO 23
<211> LENGTH: 19
<212> TYPE: DNA
<213> ORGANISM: Artificial sequence
<220> FEATURE:
<223> OTHER INFORMATION: Synthetic

<400> SEQUENCE: 23
catgaagagg gaagctgtg                                              19

<210> SEQ ID NO 24
<211> LENGTH: 19
<212> TYPE: DNA
<213> ORGANISM: Artificial sequence
<220> FEATURE:
<223> OTHER INFORMATION: Synthetic

<400> SEQUENCE: 24
ccactggtag cacattctg                                              19

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
ccagagcatg tacgccaact                                             20

<210> SEQ ID NO 26
<211> LENGTH: 20
<212> TYPE: DNA
<213> ORGANISM: Artificial sequence
<220> FEATURE:
<223> OTHER INFORMATION: Synthetic

<400> SEQUENCE: 26
cacgtcgtag agggagaagg                                             20

<210> SEQ ID NO 27
<211> LENGTH: 22
<212> TYPE: DNA
<213> ORGANISM: Artificial sequence
<220> FEATURE:
<223> OTHER INFORMATION: Synthetic

<400> SEQUENCE: 27
catccgcttt atttataggc tg                                          22

<210> SEQ ID NO 28

```
<211> LENGTH: 19
<212> TYPE: DNA
<213> ORGANISM: Artificial sequence
<220> FEATURE:
<223> OTHER INFORMATION: Synthetic

<400> SEQUENCE: 28
tagctgtcgc aatacagag                                                19

<210> SEQ ID NO 29
<211> LENGTH: 24
<212> TYPE: DNA
<213> ORGANISM: Artificial sequence
<220> FEATURE:
<223> OTHER INFORMATION: Synthetic

<400> SEQUENCE: 29
gccttggaag aagatgatgg tgta                                          24

<210> SEQ ID NO 30
<211> LENGTH: 24
<212> TYPE: DNA
<213> ORGANISM: Artificial sequence
<220> FEATURE:
<223> OTHER INFORMATION: Synthetic

<400> SEQUENCE: 30
ccttggcatt cagaatcagg agat                                          24

<210> SEQ ID NO 31
<211> LENGTH: 19
<212> TYPE: DNA
<213> ORGANISM: Artificial sequence
<220> FEATURE:
<223> OTHER INFORMATION: Synthetic

<400> SEQUENCE: 31
ctcagccttc accattact                                                19

<210> SEQ ID NO 32
<211> LENGTH: 19
<212> TYPE: DNA
<213> ORGANISM: Artificial sequence
<220> FEATURE:
<223> OTHER INFORMATION: Synthetic

<400> SEQUENCE: 32
ttctcaggaa gtgcttgtt                                                19

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
ctaagaacct gatggagaag                                               20

<210> SEQ ID NO 34
<211> LENGTH: 19
<212> TYPE: DNA
<213> ORGANISM: Artificial sequence
<220> FEATURE:
<223> OTHER INFORMATION: Synthetic

<400> SEQUENCE: 34
```
gcattggaca gaaggatat                                              19

<210> SEQ ID NO 35
<211> LENGTH: 19
<212> TYPE: DNA
<213> ORGANISM: Artificial sequence
<220> FEATURE:
<223> OTHER INFORMATION: Synthetic

<400> SEQUENCE: 35
tacaacgccc tctatgcac                                              19

<210> SEQ ID NO 36
<211> LENGTH: 23
<212> TYPE: DNA
<213> ORGANISM: Artificial sequence
<220> FEATURE:
<223> OTHER INFORMATION: Synthetic

<400> SEQUENCE: 36
caaagcgtat tcacctagtt ctc                                         23

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
agcactggtc ttgagtatcc                                             20

<210> SEQ ID NO 38
<211> LENGTH: 20
<212> TYPE: DNA
<213> ORGANISM: Artificial sequence
<220> FEATURE:
<223> OTHER INFORMATION: Synthetic

<400> SEQUENCE: 38
ctccagatgt tcttcgtggt                                             20

<210> SEQ ID NO 39
<211> LENGTH: 19
<212> TYPE: DNA
<213> ORGANISM: Artificial sequence
<220> FEATURE:
<223> OTHER INFORMATION: Synthetic

<400> SEQUENCE: 39
agagcagtca ttatggcga                                              19

<210> SEQ ID NO 40
<211> LENGTH: 19
<212> TYPE: DNA
<213> ORGANISM: Artificial sequence
<220> FEATURE:
<223> OTHER INFORMATION: Synthetic

<400> SEQUENCE: 40
cagtgttcca tcctccagg                                              19

<210> SEQ ID NO 41
<211> LENGTH: 20
<212> TYPE: DNA

```
<213> ORGANISM: Artificial sequence
<220> FEATURE:
<223> OTHER INFORMATION: Synthetic

<400> SEQUENCE: 41
gatgcacgtt aaggaagcag                                                   20

<210> SEQ ID NO 42
<211> LENGTH: 19
<212> TYPE: DNA
<213> ORGANISM: Artificial sequence
<220> FEATURE:
<223> OTHER INFORMATION: Synthetic

<400> SEQUENCE: 42
atgataccag ccacaccag                                                    19

<210> SEQ ID NO 43
<211> LENGTH: 19
<212> TYPE: DNA
<213> ORGANISM: Artificial sequence
<220> FEATURE:
<223> OTHER INFORMATION: Synthetic

<400> SEQUENCE: 43
tctaggatgg ctcctctgg                                                    19

<210> SEQ ID NO 44
<211> LENGTH: 20
<212> TYPE: DNA
<213> ORGANISM: Artificial sequence
<220> FEATURE:
<223> OTHER INFORMATION: Synthetic

<400> SEQUENCE: 44
gcaaactcct tcaggttctg                                                   20

<210> SEQ ID NO 45
<211> LENGTH: 19
<212> TYPE: DNA
<213> ORGANISM: Artificial sequence
<220> FEATURE:
<223> OTHER INFORMATION: Synthetic

<400> SEQUENCE: 45
attcctgaga atgccgagg                                                    19

<210> SEQ ID NO 46
<211> LENGTH: 19
<212> TYPE: DNA
<213> ORGANISM: Artificial sequence
<220> FEATURE:
<223> OTHER INFORMATION: Synthetic

<400> SEQUENCE: 46
tccatgttgg cactactcg                                                    19

<210> SEQ ID NO 47
<211> LENGTH: 21
<212> TYPE: DNA
<213> ORGANISM: Artificial sequence
<220> FEATURE:
<223> OTHER INFORMATION: Synthetic

<400> SEQUENCE: 47
agcagatgaa gatgtaccga g                                                 21
```

<210> SEQ ID NO 48
<211> LENGTH: 19
<212> TYPE: DNA
<213> ORGANISM: Artificial sequence
<220> FEATURE:
<223> OTHER INFORMATION: Synthetic

<400> SEQUENCE: 48
cacagagact ctcggaagc                                           19

<210> SEQ ID NO 49
<211> LENGTH: 21
<212> TYPE: DNA
<213> ORGANISM: Artificial sequence
<220> FEATURE:
<223> OTHER INFORMATION: Synthetic

<400> SEQUENCE: 49
ggactggtat ttgtgtctga g                                        21

<210> SEQ ID NO 50
<211> LENGTH: 21
<212> TYPE: DNA
<213> ORGANISM: Artificial sequence
<220> FEATURE:
<223> OTHER INFORMATION: Synthetic

<400> SEQUENCE: 50
tcagaggaca cttggattca c                                        21

<210> SEQ ID NO 51
<211> LENGTH: 19
<212> TYPE: DNA
<213> ORGANISM: Artificial sequence
<220> FEATURE:
<223> OTHER INFORMATION: Synthetic

<400> SEQUENCE: 51
aattcaatgg ccaagtcgg                                           19

<210> SEQ ID NO 52
<211> LENGTH: 20
<212> TYPE: DNA
<213> ORGANISM: Artificial sequence
<220> FEATURE:
<223> OTHER INFORMATION: Synthetic

<400> SEQUENCE: 52
agtgcaacca gtaacaaagc                                          20

<210> SEQ ID NO 53
<211> LENGTH: 21
<212> TYPE: DNA
<213> ORGANISM: Artificial sequence
<220> FEATURE:
<223> OTHER INFORMATION: Synthetic

<400> SEQUENCE: 53
acctttgatg agatcttgca g                                        21

<210> SEQ ID NO 54
<211> LENGTH: 22
<212> TYPE: DNA
<213> ORGANISM: Artificial sequence
<220> FEATURE:

<223> OTHER INFORMATION: Synthetic

<400> SEQUENCE: 54
gaagccattg atttgagttt cc                                              22

<210> SEQ ID NO 55
<211> LENGTH: 21
<212> TYPE: DNA
<213> ORGANISM: Artificial sequence
<220> FEATURE:
<223> OTHER INFORMATION: Synthetic

<400> SEQUENCE: 55
ggaatgtgat gtatgatagc c                                               21

<210> SEQ ID NO 56
<211> LENGTH: 19
<212> TYPE: DNA
<213> ORGANISM: Artificial sequence
<220> FEATURE:
<223> OTHER INFORMATION: Synthetic

<400> SEQUENCE: 56
tgatttcggt ttgttctgg                                                  19

<210> SEQ ID NO 57
<211> LENGTH: 20
<212> TYPE: DNA
<213> ORGANISM: Artificial sequence
<220> FEATURE:
<223> OTHER INFORMATION: Synthetic

<400> SEQUENCE: 57
ttacagcggt tgtgatgctc                                                 20

<210> SEQ ID NO 58
<211> LENGTH: 20
<212> TYPE: DNA
<213> ORGANISM: Artificial sequence
<220> FEATURE:
<223> OTHER INFORMATION: Synthetic

<400> SEQUENCE: 58
ggccatgtcc aagtcagagt                                                 20

<210> SEQ ID NO 59
<211> LENGTH: 20
<212> TYPE: DNA
<213> ORGANISM: Artificial sequence
<220> FEATURE:
<223> OTHER INFORMATION: Synthetic

<400> SEQUENCE: 59
cccagagctt tgcagtaacc                                                 20

<210> SEQ ID NO 60
<211> LENGTH: 20
<212> TYPE: DNA
<213> ORGANISM: Artificial sequence
<220> FEATURE:
<223> OTHER INFORMATION: Synthetic

<400> SEQUENCE: 60
cacaggacac catcaggttg                                                 20

<210> SEQ ID NO 61
<211> LENGTH: 23
<212> TYPE: DNA
<213> ORGANISM: Artificial sequence
<220> FEATURE:
<223> OTHER INFORMATION: Synthetic

<400> SEQUENCE: 61
taatgactcc gcatcttact acc                                           23

<210> SEQ ID NO 62
<211> LENGTH: 20
<212> TYPE: DNA
<213> ORGANISM: Artificial sequence
<220> FEATURE:
<223> OTHER INFORMATION: Synthetic

<400> SEQUENCE: 62
agcacatctt gctcactagg                                               20

<210> SEQ ID NO 63
<211> LENGTH: 22
<212> TYPE: DNA
<213> ORGANISM: Artificial sequence
<220> FEATURE:
<223> OTHER INFORMATION: Synthetic

<400> SEQUENCE: 63
ttcagtctcc tgggaagctg tg                                            22

<210> SEQ ID NO 64
<211> LENGTH: 23
<212> TYPE: DNA
<213> ORGANISM: Artificial sequence
<220> FEATURE:
<223> OTHER INFORMATION: Synthetic

<400> SEQUENCE: 64
tgcacttcag aaatggccga gag                                           23

<210> SEQ ID NO 65
<211> LENGTH: 19
<212> TYPE: DNA
<213> ORGANISM: Artificial sequence
<220> FEATURE:
<223> OTHER INFORMATION: Synthetic

<400> SEQUENCE: 65
ctcccaagtt caagcagag                                                19

<210> SEQ ID NO 66
<211> LENGTH: 22
<212> TYPE: DNA
<213> ORGANISM: Artificial sequence
<220> FEATURE:
<223> OTHER INFORMATION: Synthetic

<400> SEQUENCE: 66
tgtcatctcc aaatcctttc ac                                            22

<210> SEQ ID NO 67
<211> LENGTH: 20
<212> TYPE: DNA
<213> ORGANISM: Artificial sequence
<220> FEATURE:
<223> OTHER INFORMATION: Synthetic

```
<400> SEQUENCE: 67
cggattataa ataccggccc                                              20

<210> SEQ ID NO 68
<211> LENGTH: 24
<212> TYPE: DNA
<213> ORGANISM: Artificial sequence
<220> FEATURE:
<223> OTHER INFORMATION: Synthetic

<400> SEQUENCE: 68
gtgtacttat ccttcttcat gagc                                         24

<210> SEQ ID NO 69
<211> LENGTH: 20
<212> TYPE: DNA
<213> ORGANISM: Artificial sequence
<220> FEATURE:
<223> OTHER INFORMATION: Synthetic

<400> SEQUENCE: 69
cggttcatca tggtacagtc                                              20

<210> SEQ ID NO 70
<211> LENGTH: 20
<212> TYPE: DNA
<213> ORGANISM: Artificial sequence
<220> FEATURE:
<223> OTHER INFORMATION: Synthetic

<400> SEQUENCE: 70
caggagtttg agggtagctc                                              20

<210> SEQ ID NO 71
<211> LENGTH: 20
<212> TYPE: DNA
<213> ORGANISM: Artificial sequence
<220> FEATURE:
<223> OTHER INFORMATION: Synthetic

<400> SEQUENCE: 71
tggacgggca caacttcatc                                              20

<210> SEQ ID NO 72
<211> LENGTH: 20
<212> TYPE: DNA
<213> ORGANISM: Artificial sequence
<220> FEATURE:
<223> OTHER INFORMATION: Synthetic

<400> SEQUENCE: 72
gggcaggttc ttggcactct                                              20

<210> SEQ ID NO 73
<211> LENGTH: 20
<212> TYPE: DNA
<213> ORGANISM: Artificial sequence
<220> FEATURE:
<223> OTHER INFORMATION: Synthetic

<400> SEQUENCE: 73
gggaagaggt gatggaacca                                              20

<210> SEQ ID NO 74
<211> LENGTH: 20
```

```
<212> TYPE: DNA
<213> ORGANISM: Artificial sequence
<220> FEATURE:
<223> OTHER INFORMATION: Synthetic

<400> SEQUENCE: 74
aagccctgaa ccctctttgc                                              20

<210> SEQ ID NO 75
<211> LENGTH: 16
<212> TYPE: DNA
<213> ORGANISM: Artificial sequence
<220> FEATURE:
<223> OTHER INFORMATION: Synthetic

<400> SEQUENCE: 75
tcccccgcgt gaactg                                                  16

<210> SEQ ID NO 76
<211> LENGTH: 20
<212> TYPE: DNA
<213> ORGANISM: Artificial sequence
<220> FEATURE:
<223> OTHER INFORMATION: Synthetic

<400> SEQUENCE: 76
caaggcattt tgcgttcaca                                              20

<210> SEQ ID NO 77
<211> LENGTH: 22
<212> TYPE: DNA
<213> ORGANISM: Artificial sequence
<220> FEATURE:
<223> OTHER INFORMATION: Synthetic

<400> SEQUENCE: 77
ccacagcctc ctttcaataa cc                                           22

<210> SEQ ID NO 78
<211> LENGTH: 19
<212> TYPE: DNA
<213> ORGANISM: Artificial sequence
<220> FEATURE:
<223> OTHER INFORMATION: Synthetic

<400> SEQUENCE: 78
ggagtcttcg cttggggta                                               19

<210> SEQ ID NO 79
<211> LENGTH: 23
<212> TYPE: DNA
<213> ORGANISM: Artificial sequence
<220> FEATURE:
<223> OTHER INFORMATION: Synthetic

<400> SEQUENCE: 79
gggactttgc agaaaggctt cac                                          23

<210> SEQ ID NO 80
<211> LENGTH: 23
<212> TYPE: DNA
```

```
<213> ORGANISM: Artificial sequence
<220> FEATURE:
<223> OTHER INFORMATION: Synthetic

<400> SEQUENCE: 80
agactgctct gtgtttgtgt gag                                              23
```